United States Patent [19]
McMahon et al.

[11] Patent Number: 5,362,971
[45] Date of Patent: Nov. 8, 1994

[54] FIBER OPTIC DETECTION SYSTEM

[75] Inventors: Robert L. McMahon, Clayton; Robert B. McCullough, Sunol; Victor Ivashin, Pleasant Hill, all of Calif.

[73] Assignee: Terrascope Systems, Inc., Los Gatos, Calif.

[21] Appl. No.: 29,017

[22] Filed: Mar. 10, 1993

[51] Int. Cl.$^5$ .............................................. G01N 15/06
[52] U.S. Cl. ..................... 250/577; 250/904
[58] Field of Search ................... 250/577, 904, 227.25; 356/133

[56]  References Cited
U.S. PATENT DOCUMENTS

| | | | |
|---|---|---|---|
| 3,995,168 | 11/1976 | Neuscheler et al. | 250/577 |
| 4,069,838 | 1/1978 | Hansel et al. | 137/392 |
| 4,082,959 | 4/1978 | Nakashima | 250/906 |
| 4,118,634 | 10/1978 | Carvalko et al. | 250/577 |
| 4,155,013 | 5/1979 | Spiteri | 250/577 |
| 4,156,149 | 5/1979 | Vaccari | 250/577 |
| 4,287,427 | 9/1981 | Scifres | 250/577 |
| 4,351,180 | 10/1982 | Harding | 340/619 |
| 4,668,870 | 5/1987 | Okura | 250/577 |
| 4,689,484 | 8/1987 | McMahon | 250/227 |
| 5,200,628 | 4/1993 | Ikeda et al. | 250/577 |
| 5,239,175 | 8/1993 | Jawad et al. | 250/577 |

Primary Examiner—David C. Nelms
Attorney, Agent, or Firm—Jack M. Wiseman

[57]  ABSTRACT

A fiber optic detection system in which a single optic fiber has a U-shaped configuration. A source of light is disposed at one upper free end of the optic fiber and a light detector is disposed at the other upper free end of the optic fiber. At the bottom of the optic fiber is a light variable loop adapted to be disposed in various media, such as liquids, fluids and air. The light from the source of light is conducted from the source of light through the optic fiber and to the light detector. The quantum of light lost as the light travels through the light variable loop will depend on the medium or the concentration of the medium in which the light variable loop is disposed. The light detector detects the light advancing thereto to produce a signal representative of the medium or the concentration of the medium in which the light variable loop is disposed. An electronic circuit with a microprocessor is responsive to the signal produced by the light detector for determining the medium or the concentration of the medium in which the light variable loop is disposed.

24 Claims, 9 Drawing Sheets

FIBER OPTIC DETECTION SYSTEM

BACKGROUND OF THE INVENTION

The present invention relates in general to fiber optic detection systems, and more particularly to a fiber optic detection system employing a single fiber optic element.

The patent to McMahon, U.S. Pat. No. 4,689,484, issued on Aug. 25, 1987, for Photoelectric Leak Detection System For Double-Walled Tanks And The Like discloses a photoelectric leak detection system for a double-walled tank in which a pair of optical fibers extend from the top to the bottom of a double-walled tank within the space between the walls. At the lower ends of the optical fibers are respective probes. A light source is positioned at the upper end of one of the optical fibers and a photodiode is disposed at the upper end of the other optical fiber to detect changes in the reflected light conducted through the other optical fiber. The leak detector uses a transparent body at the terminal ends of the optical fibers and a spacer support for maintaining the terminal ends of the optical fibers and the transparent body above the bottom of the tank.

In the patent to Hansel et al., U.S. Pat. No. 4,069,838, granted on Jan. 24, 1978, for Fiber Optic Liquid Level Sensor, there is disclosed a liquid level sensor employing a single fiber optic tube. At one end of the fiber optic tube is a source of light. At the other end of the fiber optic tube is a light detection device. The fiber optic tube is interrupted to form a gap section with a pair of gaps. Light is cast onto liquid through one gap and refracted light passes through the other gap to be sensed by the light detection device. When the liquid in a container rises into the gap, the light passing through the fiber optic tube is interrupted.

In the patent to Robert C. Harding, U.S. Pat. No. 4,354,180, issued on Oct. 12, 1982, for Electro-Optical Liquid Level Sensor, there is disclosed a liquid level sensing device in which there is a light conductor and an electrical conductor. A source of light is located at the upper end of the light conductor and an electro-optical transducer is located at the lower end of the light conductor. One electro-optical transducer at the lower end of the light conductor casts a beam of light toward liquid through a transparent probe. The electro-optical transducer at the lower end of the light conductor is disposed in spaced relation to the probe. Another electro-optical transducer is disposed in spaced relation to the probe for receiving reflected light passing through the transparent probe. The other electro-optical transducer is connected to the electrical conductor. The beam of light is constantly reflected toward the light detecting transducer regardless of whether the probe is above the liquid or immersed in the liquid. The amplitude of the signal transmitted by the light detecting transmitter is greater when the probe is above the level of the liquid and is lesser when the probe is immersed in the liquid. The probe uses a transparent body having an index of refraction.

The patent to Neuscheler et al., U.S. Pat. No. 3,995,168, issued on Nov. 30, 1976, for Electro Optical Fluid Measurement System, discloses a device for the remote display of the level of a liquid and specific density of the liquid contained within a tank. The device includes a pair of fiber optic bundles. One fiber optic bundle conducts light from a source to be cast toward liquid in a tank. The other fiber optic bundle receives reflected light and conducts the reflected light to phototransistors. The terminal ends of the fiber optic bundles are held by a plate and form confronting faces at an angle of 45°. A prism is disposed in the space formed by the confronting surfaces of the terminal ends of the fiber optic bundles. When light detected by the other fiber optic bundle is reflected by the level of liquid being below the prism, the phototransistors will produce a signal indicating the level of the liquid is below the prism.

In the patent to Spiteri, U.S. Pat. No. 4,155,013, issued on May 15, 1979, for a Liquid Level Indicator, there is disclosed a liquid level monitor having a pair of fiber optic cables. Light from a source of light is conducted through one of the fiber optic cables. The fiber optic cables terminate in a prism within a probe. The prism is immersed in oil. The absence of oil causes the light conducted through the one fiber optic cable to impinge on a face of the prism at an angle greater than a critical angle. Light is reflected through the prism and emitted from another face of the prism to be conducted through the other fiber optic cable. If the prism is above the oil level, the light is totally reflected for conduction through the other fiber optic cable. When the prism is immersed in oil, the light is not reflected by the prism surface.

The patent to Vaccari, U.S. Pat. No. 4,156,149, granted on May 22, 1979, for Optical Material Level Probe, discloses an optical level detection probe having spaced apart guides mounted on an epoxy support. Each guide has a 45° angle reflecting face and the reflecting faces oppose one another. When material reaches the reflecting surfaces, the light is not transmitted from one guide to the other guide. When material is below the reflecting surfaces, light travels from one reflecting surface to the other reflecting surface to be detected by a light sensor.

SUMMARY OF THE INVENTION

A fiber optic detection system in which an optic fiber element has a source of light at one end thereof and a light detector at the other end thereof. Intermediate the ends of the optic fiber element is a continuous and uninterrupted light variable section. The quantum of light passing from the light variable section to the light detector will change depending on the medium and/or the concentration of the medium in which the light variable section is disposed. The amplitude of the signal produced by the light detector will vary dependent on the quantum of light sensed by the light detector. An electronic circuit having a microcomputer responsive to the signal produced by the light detector determines the medium or the concentration of the medium in which the light variable section is disposed.

A fiber optic detection system in which an optic fiber element has a source of light at one end thereof and a light detector at the other end thereof. Intermediate the ends of the optic fiber element is a continuous and uninterrupted light variable loop. The quantum of light passing from the light variable loop to the light detector will change dependent on the medium and/or the concentration of the medium in which the light variable loop is disposed. The amplitude of a signal produced by the light detector will vary dependent on the quantum of light sensed by the light detector. An electronic circuit having a microcomputer responsive to the signal produced by the light detector determines the medium or the concentration of the medium in which the light variable section is disposed.

A fiber optic detection system in which a single optic fiber element has a source of light at one end thereof and a light detector at the other end thereof. Intermediate the ends of the single optic fiber element is a light variable loop. The quantum of light passing from the light variable loop to the light detector will change dependent on the medium and/or concentration of the medium in which the light variable loop is disposed. The amplitude of a signal produced by the light detector will vary dependent on the quantum of light sensed and detected by the light detector. An electronic circuit having a microcomputer responsive to the signal produced by the light detector determines the medium or the concentration of the medium in which the light variable section is disposed.

A fiber optic detection system in which a single optic fiber element has a source of light at one end thereof and a light detector at the other end thereof. Intermediate the ends of the single optic fiber element is a light variable loop. The single optic fiber element is surrounded by an opaque means except at the light variable loop thereof. The quantum of light passing from the light variable loop to the light detector will change dependent on the medium and/or the concentration of the medium in which the light variable loop is disposed. The amplitude of a signal produced by the light detector will vary dependent on the quantum of light sensed and detected by the light detector. An electronic circuit includes a microcomputer responsive to the signal produced by the light detector determines the medium or the concentration of the medium in which the light variable section is disposed.

A feature of the present invention is the fiber optic detection system uses a single optic fiber element with a light variable section intermediate the ends thereof, and the quantum of light advanced through the light variable section changes in accordance with the light losses resulting from the characteristics of the medium or the concentration of the medium in which the light variable section is disposed.

Another feature of the present invention is the fiber optic detection system obviates the need for a probe using prisms, glass plates, gap sections, light refracting transparent bodies, and support structures for spacing at the lowermost end of the fiber optic elements.

Another feature of the present invention is the fiber optic detection system in which an optic fiber element has a light variable loop intermediate the ends thereof and the radius of the arcuate portion of the loop is of a predetermined radius for detecting the substance in which the loop is disposed by sensing and detecting light loss of the light passing through the loop.

Another feature of the present invention is the fiber optic leak detection system uses an optic fiber element that has a source of light at one end thereof and a light detector at the other end thereof for detecting changes in light losses resulting from a light variable section thereof disposed in different media or different concentrations of the same medium.

Another feature of the present invention is the fiber optic leak detection system uses an optic fiber element that has a source of light at one end thereof and a light detector at the other end thereof for detecting differences in quantum of light resulting from a light variable section thereof disposed in media or concentrations of the same medium having different indices of light refraction.

Another feature of the present invention is that the fiber optic detection system discriminates between different fluids, not merely the detection of the presence or absence of a fluid, as long as the fluid has an index of refraction.

Briefly described, a fiber optic detection system in which a single optic fiber element has a U-shaped configuration. A source of light is disposed at one end of the optic fiber element and a light detector is disposed at the other end of the optic fiber element. The optic fiber element extends downwardly into a container and the longitudinally extending legs of the optic fiber element are surrounded by respective opaque means. Adjoining the lower ends of the legs of the optic fiber element is a light variable loop section of the fiber optic element, which is not covered by any opaque means. The light variable loop is adapted to be disposed in various media, such as liquids, fluids, air and the like. The light from the source of light is conducted from the source of light, through the optic fiber element and to the light detector. The quantum of light travelling through the light variable loop or the light loss resulting from travelling through the light variable loop will depend on the medium and/or different concentrations of the same medium in which the light variable loop is disposed. The quantum of light travelling through the light variable loop will decrease as light escapes from the light variable loop. The quantum of light escaping from the light variable loop will be greater when the light variable loop is disposed in a gas or fluid having an index of refraction higher than the index of refraction of air. Thus, the quantum of light advancing beyond the light variable loop provides a measurement of the index of refraction of the gas or fluid in which the light variable loop is disposed. The light detector senses and detects the light advancing thereto to produce a signal representative of the medium or concentrations of the same medium in which the light variable loop is disposed. An electronic circuit has a microprocessor responsive to the signal produced by the light detector determines the medium or the concentration of the medium in which the light variable loop is disposed.

DETAILED DESCRIPTION OF THE PREFERRED EMBODIMENT

Figure 1:
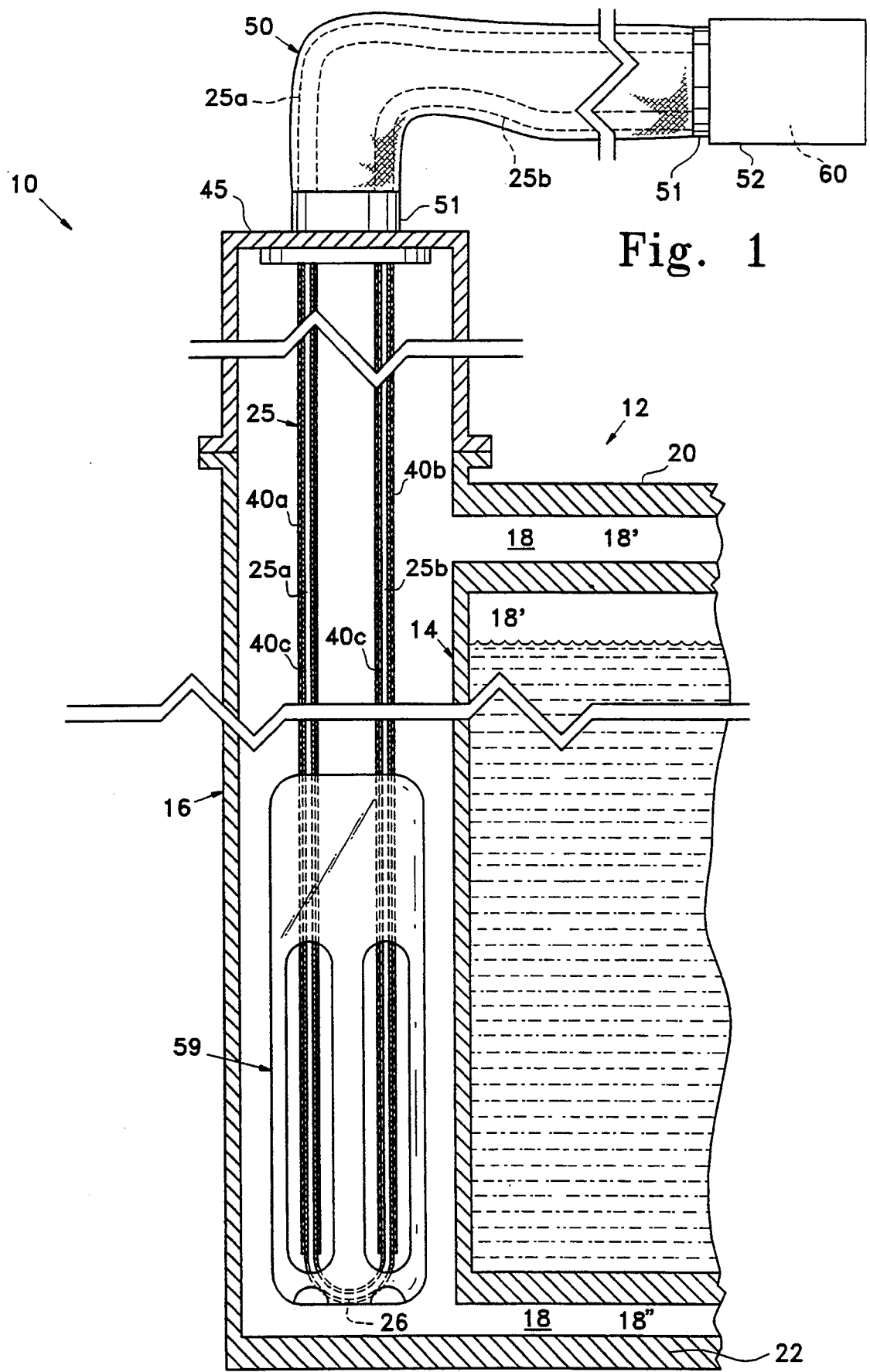
FIG. 1 is a diagrammatic fragmentary, elevational sectional view of a double-walled tank in which is partially disposed a fiber optic detection system embodying the present invention.

Illustrated in FIG. 1 is a fiber optic element 25 of a fiber optic substance detection system 10 embodying the present invention. The fiber optic substance detection system 10, in the exemplary embodiment, is adaptable for use in a double-walled tank 12. In a well-known manner, the double-walled tank 12 comprises an inner tank 14 and an outer tank 16. The inner tank 14 is disposed within the outer tank 16 as to define an interspace 18 therebetween. The interspace 18 is an annular space or an annulus. The annulus 18 has an upper discoid space 18' and a lower discoid space 18". The outer tank 16 includes a top plate 20 and a bottom plate 22.

The fiber optic substance detection system 10 comprises, in the preferred embodiment, the single optic fiber element 25. In the exemplary embodiment, the optic fiber element 25 is a plastic fiber and is one millimeter in diameter. The fiber optic element 25 may be an individual optic fiber, a bundle of optic fibers, a cable of optic fibers, a tube of optic fibers, or the like. The optic fiber element 25, in the exemplary embodiment, extends from the top of the double-walled tank 12 to the bottom of the double-walled tank 12 so as to be disposed at the lower end thereof in the annulus 18 adjacent the discoid space 18" and continues upwardly to the top of the double-walled tank 12. Intermediate the ends of the optic fiber element 25 is a transparent, arcuate light variable section 26.

In the preferred embodiment, the optic fiber element 25 is in the form of a cable of optic fiber and has a generally U-shape configuration with longitudinal extending legs 25a and 25b. Adjoining the lower ends of the legs 25a and 25b, in the preferred embodiment, is the light variable loop 26 of the optic fiber element 25. The legs 25a and 25b of the fiber optic element 25 and the light variable loop 26 of the fiber optic element 25 are made of optic fiber material. The light variable loop 26, in the preferred embodiment, is located midway between the free ends of the fiber optic element 25 and is disposed at the bottom of the double-walled tank 12. In the exemplary embodiment, the optic fiber element is the Super Eska plastic optical fiber cable sold by Mitsubishi Rayon Co. Ltd. of Tokyo, Japan, as part No. SH 4001. The Super Eska plastic optical fiber cable sold by Mitsubisihi Rayon Co. Ltd. is a step-index type of optical fiber comprising a core of high-purity polymethyl methacrylate polymer and a thin layer of fluorine polymer cladding. The light variable loop 26, is free of an opaque jacket, but, in the exemplary embodiment, does have a cladding through which light may be transmitted.

The configuration of the light variable loop 26, in the exemplary embodiment, is formed by a heating process. A section of the fiber optic element 25 free of the opaque jacket, for example the Super Eska plastic optical fiber cable sold by Mitsubishi Rayon Co. as part No. SH 4001, is immersed in water heated to a suitable temperature between 170° Fahrenheit and 190° Fahrenheit for approximately 4 to 5 minutes to form a predetermined radius. After the light variable loop 26 has formed a predetermined radius, the light variable loop 26 is removed from the heated water and allowed to cool to ambient temperature. Thereupon, the light variable loop 26 has a permanent desired configuration and predetermined radius. The heating temperature and heat exposure time may vary dependent on the optic fiber material, fiber diameter and desired loop configuration.

Figure 2:
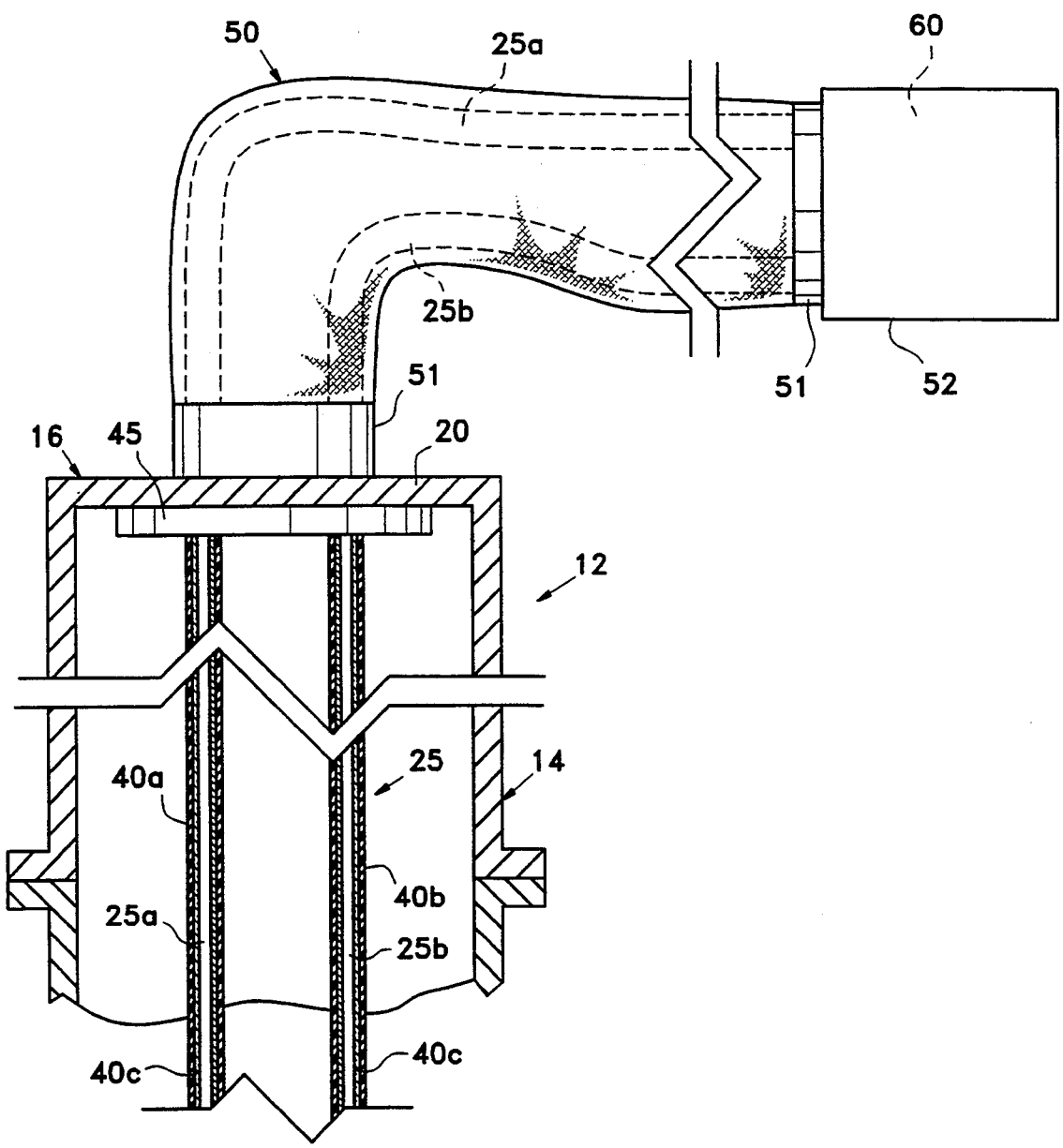
FIG. 2 is a diagrammatic enlarged, fragmentary, elevational sectional view of the double-walled tank shown in FIG. 1 in which is disposed the upper end of a fiber optic element of the fiber optic detection system partially shown in FIG. 1.
Figure 3:
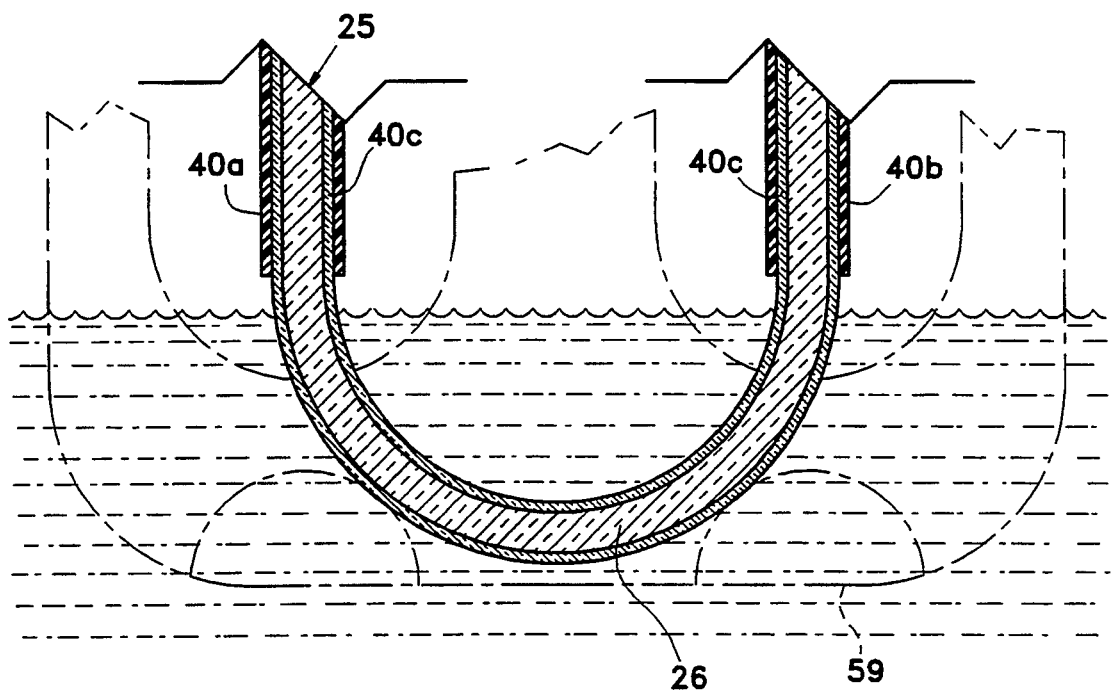
FIG. 3 is a diagrammatic enlarged, fragmentary, elevational sectional view of the lower end of the fiber optic element of the fiber optic detection system shown in FIGS. 1 and 2 illustrated with the light variable loop thereof immersed in a liquid contained in the double-walled tank shown in FIGS. 1 and 2.
Figure 4:
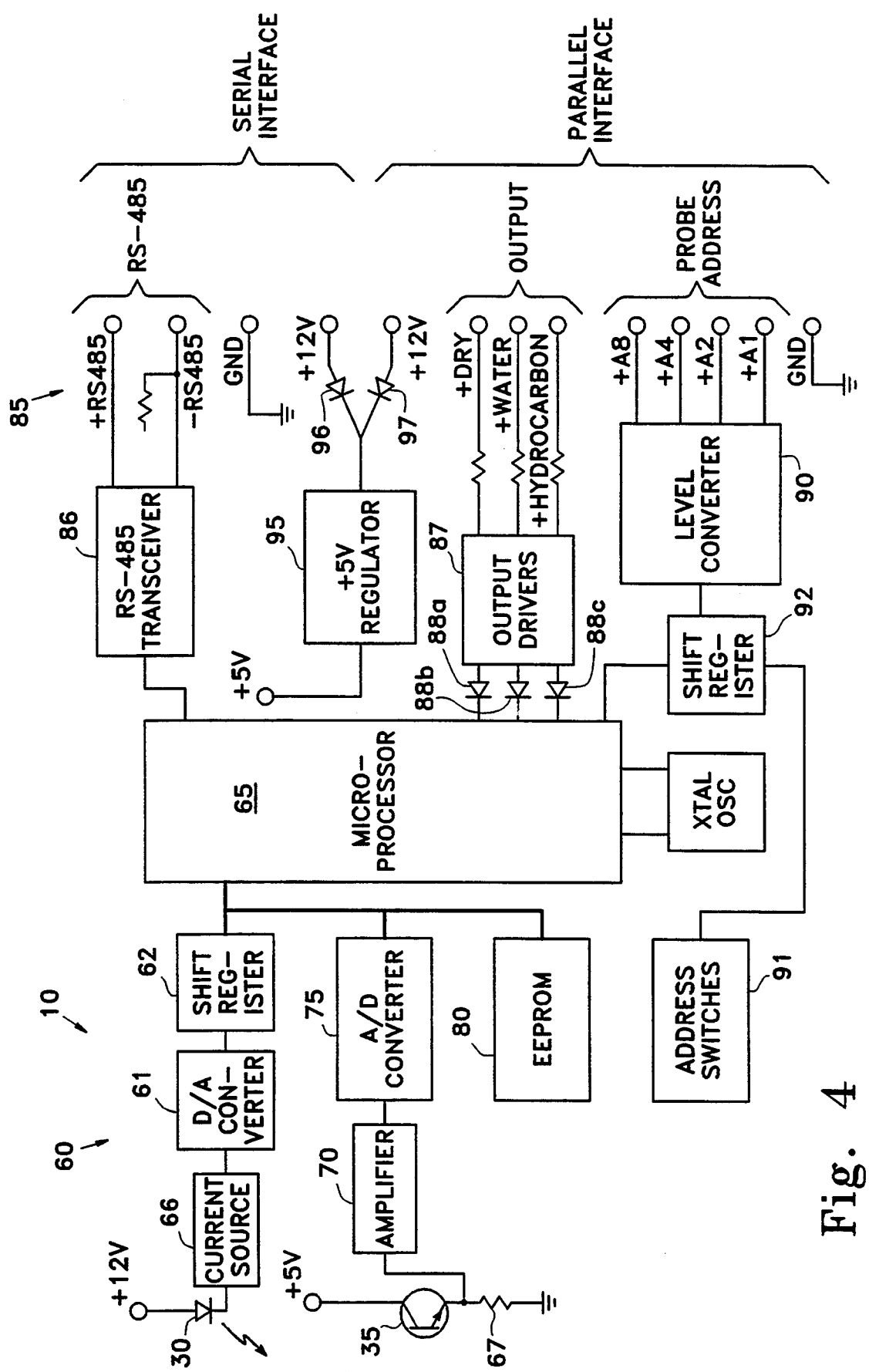
FIG. 4 is a block diagram of an electronic circuit for the fiber optic detection system embodying the present invention.
Figure 5:
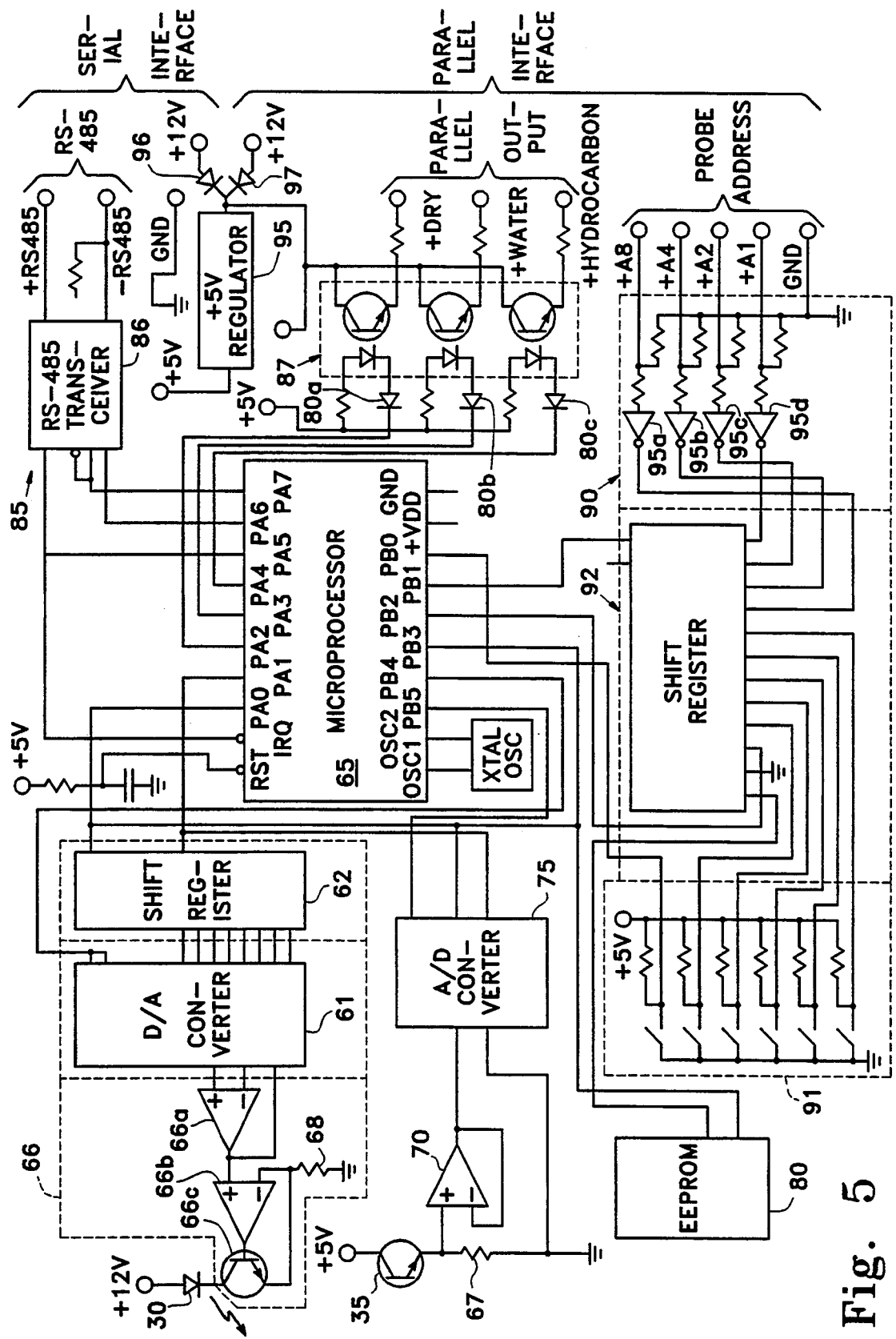
FIG. 5 is a schematic diagram of the electronic circuit shown in FIG. 4 for the fiber optic detection system embodying the present invention.

At one free end of the optic fiber element 25 is a suitable source of light 30 (FIGS. 4 and 5). In the exemplary embodiment, the source of light 30 is a light emitting diode, such as the light emitting diode manufactured by Motorola Semiconductor of Phoenix, Ariz., as the MFOE76. At the other free end of the optic fiber element 25 is a suitable light detector 35, such as a conventional phototransistor or photodiode. A suitable light detector is the MFOD72 manufactured by Motorola Semiconductor of Phoenix, Ariz. The source of light 30 and the light detector 35, in the exemplary embodiment, are remotely located with respect to the tank 12. Optionally, the longitudinal extending legs 25a and 25b of the optic fiber element 25 (FIGS. 2 and 3) are surrounded by respective tubular opaque jackets 40a and 40b. Between the optic fiber element 25 and the associated jackets 40a and 40b is a tubular clad 40c. The tubular clad 40c surrounds the entire optic fiber element 25 including the light variable loop 26. The Mitsubishi Rayon Co. Ltd. plastic optical fiber cable, part No. SH 4001, includes a polymer cladding. The light variable loop 26, which is not covered by any opaque jacket, is adapted to be disposed in a liquid, fluid, air and the like. Light escapes from the light variable loop 26 into the medium in which it is disposed.

While reference herein is made to clad 40c, it is apparent that the light variable loop 26 may be free of any coating or cladding. The opaque jackets 40a and 40b are employed to provide protection to the longitudinally extending legs 25a and 25b of the optic fiber element 25.

Light is conducted from the light emitting diode 30 through the optic fiber element 25 and to the phototransistor 35. The light variable loop 26 is adapted to be disposed in various media, such as a liquid (FIG. 3), a fluid, air (FIG. 1), and the like. The quantum of light travelling through the light variable loop 26 and detected by the phototransistor 35 is dependent on the medium or the concentration of the medium in which the light variant loop 26 is disposed.

The quantum of light travelling through the light variable loop 26 will decrease as light escapes from the light variable loop 26. The quantum of light escaping from the light variable loop 26 will increase when the light variable loop 26 is disposed in a gas or liquid having an index of refraction higher than the index of refraction of air. Hence, the quantum of light lost while travelling through the light variable loop 26 and the quantum of light detected by the phototransistor 35 is dependent on the medium or the concentration of the medium in which the light variable loop 26 is disposed. Thus, the quantum of light advancing beyond the light variable loop 26 provides a measurement of the index of refraction of the gas or fluid in which the light variable loop 26 is disposed. The phototransistor 35 produces a signal representative of the medium or the concentration of the medium in which the light variable loop 26 is disposed. Thus, the quantum of light lost or the quantum of light escaping while travelling through the light variable loop 26 will depend on, or will be related to, the medium or the concentration of the medium in which the light variable loop 26 is disposed. Hence, the signal produced by the phototransistor 35 will represent the medium or the concentration of the medium in which the light variable loop 26 is disposed, as long as the index of refraction can be measured.

Figure 9:
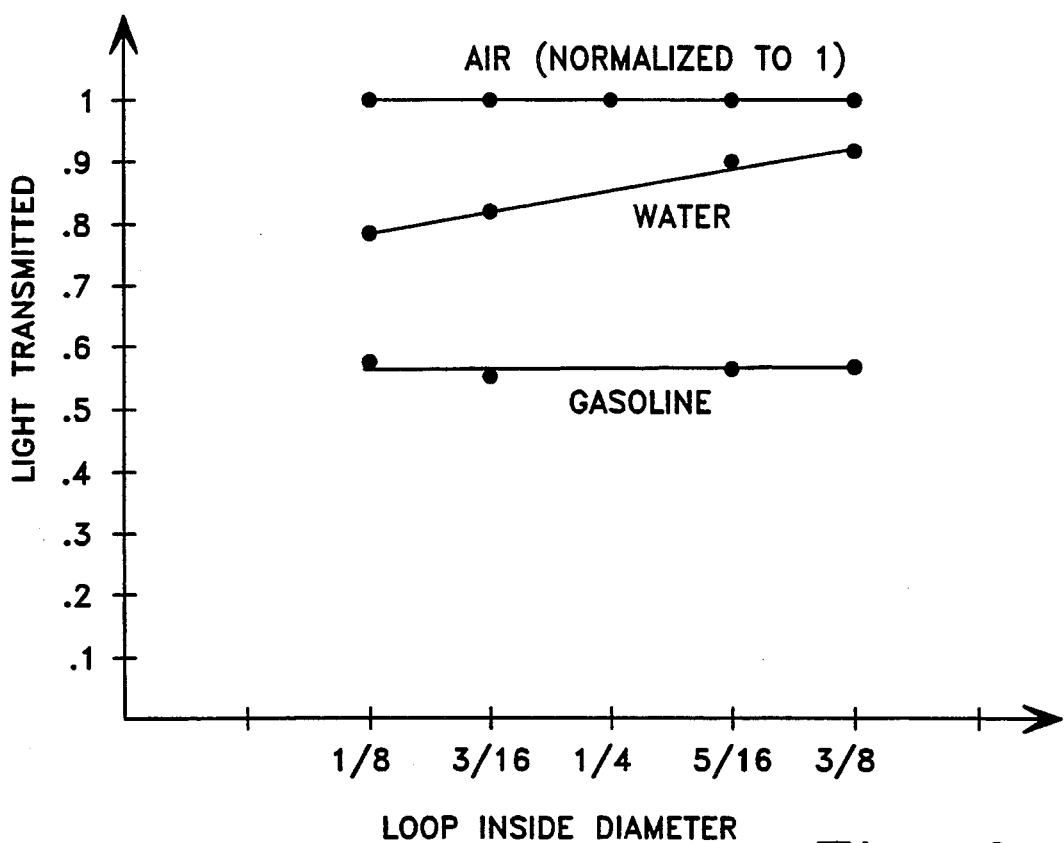
FIG. 9 is a graphical illustration of light transmitted versus loop diameter of the light variable loop of the fiber optic element for various fluids of different indices of refraction.

In the preferred embodiment, the light variable loop 26 has the same predetermined radius over the entire arcuate section of the light variable loop 26. The dimension of the radius of the light variable loop 26 is selected to produce a recognizable light detection for sensing different media in which the light variable loop 26 may be disposed, and to determine the substance or material in which the light variable loop 26 is disposed. In the exemplary embodiment, the light variable loop 26 has an inner diameter in the range of ⅛ inch to ⅝ inch to discriminate between fluids, such as air, water and gasoline. FIG. 9 illustrates graphically the light transmitted through the light variable loop 26 versus the inside loop diameter of the light variable loop 26 for various media, such as air, water and gasoline. When the light variable section 26 is curved, the amount of light that is lost, or escapes throughout the curve, is determined by the degree of curvature of the light variable loop 26. The quantum of light that is lost, or escapes from the curved light variable loop 26 of a predetermined diameter, depends on the index of refraction of the medium in which the light variable section 26 is disposed. Thus, the light loss measurement through the light variable section 26 of a predetermined curvature is not only indicative of the index of refraction of the medium in which the light variable section 26 is disposed but, also, determines the medium or the concentration of the medium in which the light variable section 26 is disposed.

Light continuously travels through the optic fiber element 25 and it is the quantum of light that is detected by the phototransistor 35 which varies dependent on the medium or the concentration of the medium in which the light variable loop 26 is disposed. There is a continuous detection of light by the phototransistor 35. The quantum of light detected by the phototransistor 35 less the loss of light resulting from the light travelling through the optic fiber element 25 and a predetermined light loss resulting from the light travelling through the light variable loop 26 while disposed in air or the like that provides a baseline value for the operation of the fiber optic detection system 10. In this manner, the fiber optic detection system 10 is monitored for accuracy and is self-checking and is fail safe.

The optic fiber element 25 is sealed against intrusion of the outside atmosphere by means of a suitable conduit 50 with plugs 51 with a compression grip at each end thereof and a suitable housing 52 for an electronic circuit 60 to be described hereinafter. The light emitting diode 30 is juxtaposed with the free end of the leg 25a of the optic fiber element 25 within the housing 52 and the phototransistor 35 is juxtaposed with the free end of the leg 25b of the optic fiber element 25 within the housing 52. Suitable aligning pins, or the like, align the free ends of the legs 25a and 25b of the optic fiber element 25 with the light emitting diode 30 and the phototransistor 35, respectively.

In the exemplary embodiment, a protective cover 59 (FIGS. 1 and 3) surrounds the light variable loop 26 of the optic fiber element 25, which includes suitable slots or gaps so as to dispose and expose the light variable loop 26 in and to the medium. The protective cover 59 has a dual side-by-side generally tubular configuration. The protective cover 59, in the preferred embodiment, is made of suitable plastic, such as Delrin, and holds the light variable loop 26 in place by channels therein. The optic fiber element 25 is caused to adhere to the protective cover 59 by a suitable adhesive, such as an epoxy. The optic fiber element 25 is secured within the protective cover 59 before the protective cover 59 is closed. The protective cover 59 protects the light variable loop 26 against scratches, nicks, or the like which may influence the quantum of light detected by the phototransistor 35.

Illustrated in FIG. 4 and 5 is the electronic circuit 60 for translating the signal transmitted from the phototransistor 35 with an electronic interface circuit 85 for use with a suitable host system, not shown. The electronic circuit 60 comprises a conventional digital-to-analog converter 61, which adjusts the intensity of the light emitted by the light emitting diode 30 under the control of a suitable microprocessor 65 microcomputer or the like, such as the 68HC 705 J2 microprocessor manufactured by Motorola Semiconductor of Phoenix, Ariz. A suitable digital-to-analog converter may be of the type manufactured by Texas Instruments of Dallas, Tex., as the 7524. Interconnecting the microprocessor 65 and the digital-to-analog converter 61 is a conventional parallel-in-series-out shift register 62, such as the 74HC164 manufactured by Texas Instruments of Dallas, Tex. The output of the digital-to-analog converter 61 is connected to a suitable current source 66 which includes suitable amplifiers 66a and 66b connected in series. The output of the amplifier 66b is applied to a suitable NPN transistor 66c, which, in turn, is connected to the light emitting diode 30. The transistor 66c and a resistor 68 provide a current source for controlling the brightness of the light emitting diode 30. In the exemplary embodiment, the amplifiers 66a and 66b are of the type manufactured by National Semiconductor of Santa Clara, Calif., as the LM324 amplifiers. The transistor 66c is of the type manufactured by Motorola Semiconductor of Phoenix, Ariz., as the 2N3904.

The output of the current source 66 is applied to the light emitting diode 30 to regulate the current flow through the light emitting diode 30 for adjusting the intensity of light emitted by the light emitting diode 30. In this manner, the microprocessor 65 regulates the intensity of the light emitted from the light emitting diode 30 to accommodate different lengths of the optic fiber element 25 and to allow for manufacturing variations. The current setting resistor 68 is connected to the emitter electrode of the transistor 66c.

The phototransistor 35 produces a current flow therethrough that is representative of or proportional to the quantum of light sensed by the phototransistor 35. The current flow through the phototransistor 35 flows through a load resistor 67, which is connected to the emitter electrode of the phototransistor 35. The resulting voltage across the resistor 67 is applied to a suitable amplifier 70, which may be of the type manufactured by National Semiconductor of Santa Clara, Calif., as the LM324 amplifier. The output of the amplifier 70 is applied to a conventional analog-to-digital converter 75, which may be of the type manufactured by Texas Instruments of Dallas, Tex., as the ADC0831 analog-to-digital converter. The output of the analog-to-digital converter 75 is applied to the microprocessor 65 for measuring the quantum of light detected by the phototransistor 35. In this manner, the microprocessor 65 can distinguish between various media and the concentration of the same medium in which the light variable loop 26 is disposed.

For recording the setting of the digital-to-analog converter 61 and for recording the reading from the analog-to-digital converter 75, a conventional non-volatile electrically eraseable programmable read/only memory 80 is employed. A suitable electrically erasable programmable read/only memory is of the type manufactured by National Semiconductor of Santa Clara, Calif., as the 24C02. The electrically eraseable programmable read/only memory 80 is under the control of the microprocessor 65 for storing calibration data.

The quantum of light sensed by the phototransistor 35 will decrease as light escapes or is lost in the light variable loop 26. The quantum of light ecaping or lost in the light variable loop 26 will increase when the light variable loop 26 is disposed in a gas or fluid (FIG. 3) when compared to the light variable loop 26 being disposed in air (FIG. 1). The index of light refraction for gasoline or liquid is higher than the index of light refraction for air. Thus, the quantum of light sensed by the phototransistor 35 provides a measure of the index of light refraction of the medium in which the light variable loop 26 is disposed. The microprocessor 65 determines the medium in which the light variable loop 26 is disposed by reading the output of the analog-to-digital converter 75, which is representative of the quantum of light sensed and detected by the phototransistor 35.

Connected to the microprocessor 65 is an interface circuit 85 which interfaces the microprocessor 65 with the host system, not shown. Should the host system be remotely located with respect to the fiber optic detection system 10, then a suitable transceiver 86, such as a RS-485 transceiver, will transmit serial data over an RS-485 link to a host system. Should the host system be a parallel link system, then output drivers 87 interconnect the microprocessor 65 with the parallel link system through diodes 88a-88c. In the exemplary embodiment, the output drivers 87 are conventional optoisolators.

The host parallel system sends a probe address to the fiber optic detection system 10, which probe address is compared by the microprocessor 65 to the setting of address switches 91. In the exemplary embodiment, 12 volt parallel probe addresses are applied to level converters 90, such as the 74HC4049 manufactured by Motorola Semiconductor of Phoenix, Ariz., to produce, in the exemplary embodiment, 5 volt logic signals. The microprocessor 65 reads the parallel probe address and address switches 91 through a suitable parallel-in-series-out shift register 92, such as a 74HC165 manufactured by Texas Instruments of Dallas, Tex. The microprocessor 65 compares the parallel probe address to the address switches 91 and, if they match, sends an answer on the parallel output.

In the exemplary embodiment, the electronic circuit 60 employs 12-volt direct current source of power. A conventional 5-volt voltage regulator 95 has applied thereto, in the exemplary embodiment, the 12-volt direct current voltage through diodes 96 and 97.

Figure 6A:
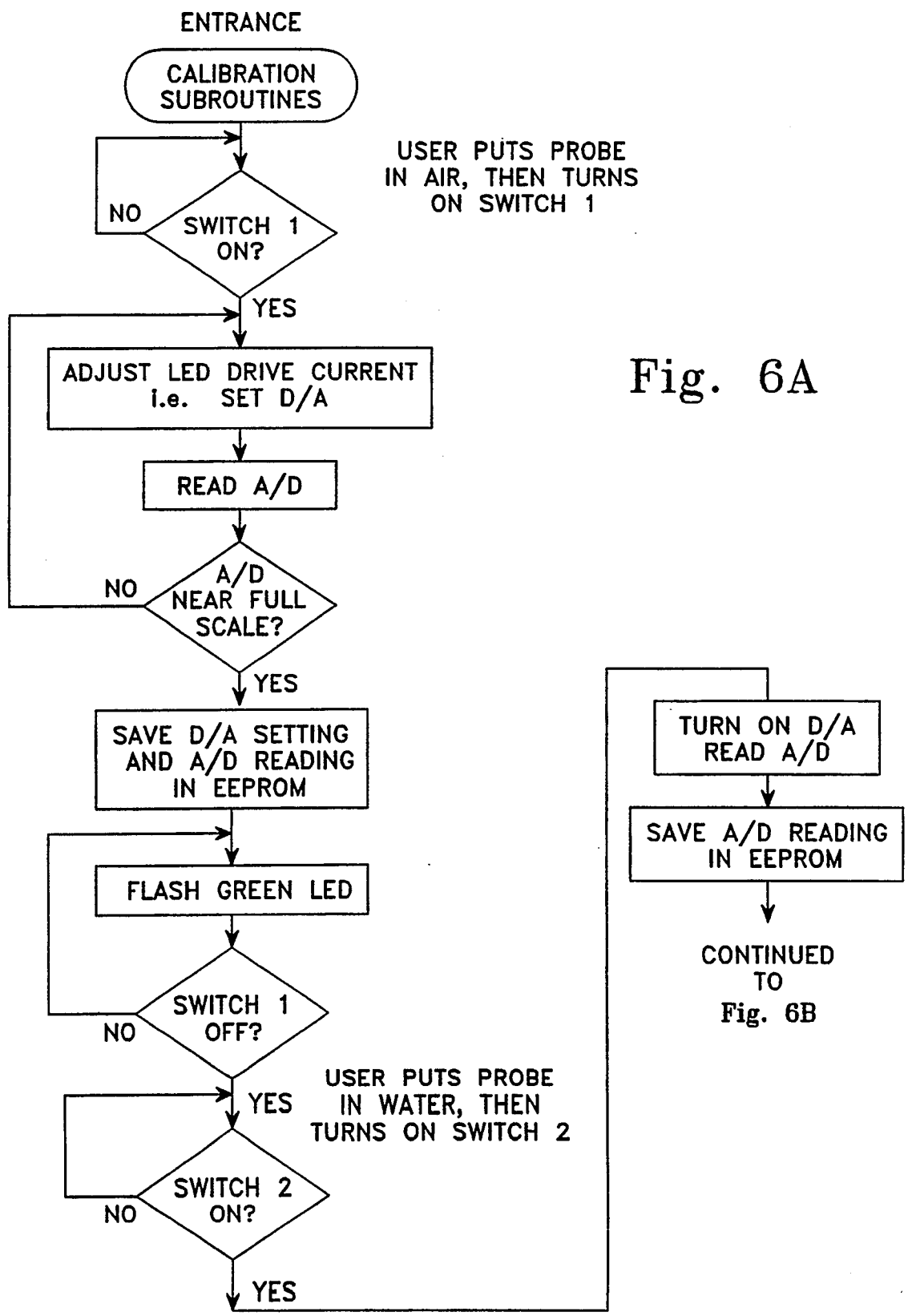
FIGS. 6A and 6B illustrate a flow diagram for the operation sequence of the electronic circuit shown in FIGS. 4 and 5 to calibrate the fiber optic detection system.
Figure 6B:
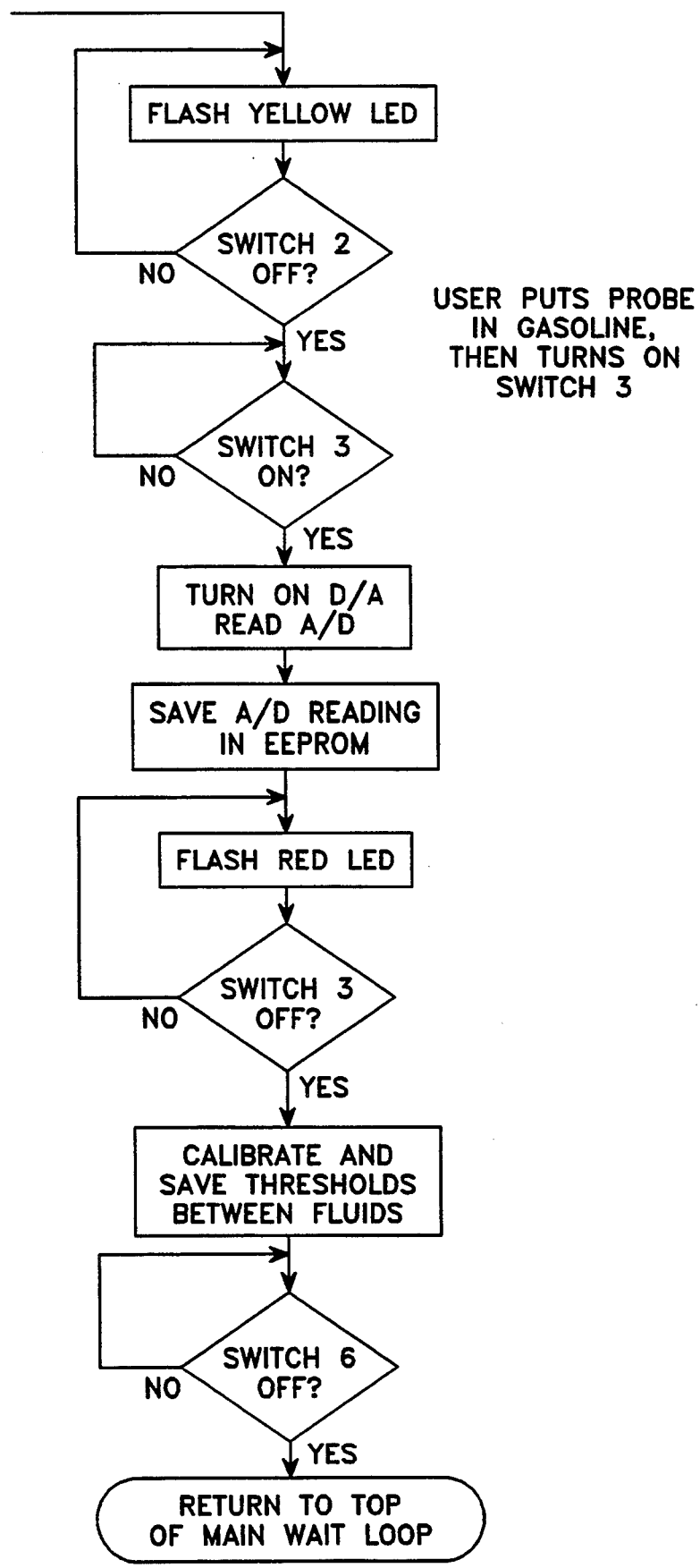

As illustrated in the flow diagrams (FIGS. 6A and 6B) for operation sequence and decisions, the optic fiber element 25 and the electronic circuit 60 are calibrated as a unit to minimize the effect of variations in cable length, and manufacturing parts and tolerances. The calibration is repeated when an optic fiber element 25 is replaced or the electronic circuit 60 is changed. The calibration is initiated by measuring the output of the analog-to-digital converter 75 when the light variable loop 26 is disposed in air (FIG. 1). Toward this end, the microprocessor 65 upon command adjusts the current flow in the light emitting diode 30 to produce just under a full scale reading on the analog-to-digital converter 75. The setting of the digital-to-analog converter 61 and the reading in the output of the analog-to-digital converter 75 is recorded in the electrically eraseable programmable read/only memory 80.

The digital-to-analog converter 61 setting will be used to set the current flow through the light emitting diode 30 for testing the medium in which the light variable loop 26 is disposed. Subsequently, the current through the light emitting diode 30 is discontinued or interrupted and the microprocessor 65 measures the dark current in the phototransistor 35. This measurement is also recorded in the electrically eraseable programmable read/only memory 80 and is compared with subsequent dark current measurements to assist in zeroing out the effects of temperature and aging of the fiber optic light detection system 10.

The light variable loop 26 is subsequently immersed in water (FIG. 3) and the microprocessor 65 reads the output of the analog-to-digital converter 75 and records the reading in the electrically eraseable programmable read/only memory 80. The light variable loop 26 is subsequently immersed in gasoline and the microprocessor 65 reads the output of the analog-to-digital converter 75 and records the reading in the electrically eraseable programmable read/only memory 80. This process can be repeated for as many different media or fluids as desired. The microprocessor 65 detects the analog-to-digital characteristics for each different medium or fluid and records the reading in the electrically eraseable programmable read/only memory 80.

After the initial calibration, the microprocessor 65 compares all readings of the output of the analog-to-digital converter 75 to the known readings recorded in the electrically eraseable programmable read/only memory 80 to transmit signals representative of the medium in which the light variable loop is disposed. The optic fiber element 25 and the electronic circuit 60 are calibrated together as a unit before use in order to minimize the effects of cable length, and manufacturing and parts tolerances.

Initially, the digital to analog converter 61 is adjusted to regulate the current flow in the light emitting diode 30 and thereby regulates the quantum of light emitted by the light emitting diode 30. This adjustment is carried out while the light variable loop 26 is disposed in air, since the light loss from the light variable loop 26 will be at a minimum. While the light variable loop 26 is disposed in air, an operator turns-on a first switch to instruct the microprocessor 65 to calibrate the fiber optic detection system 10 as a unit. When the first switch is turned-on, the microprocessor 65 adjusts the digital-to-analog converter 61 and reads the resulting voltage of the phototransistor 35 from the output of the analog-to-digital converter 75. The adjustment of the digital-to-analog converter 61 is made bit by bit until the reading from the output of the analog-to-digital converter 75 is slightly less than full scale. This setting assures the maximum accuracy in the measurements and assures the phototransistor 35 is operating in its linear range and not in saturation.

The microprocessor 65 readings of the adjustments of the digital-to-analog converter 61 and the analog-to-digital converter 75 output for air are recorded in the electrically eraseable programmable read/only memory 80 as calibration values to be used for future measurements. The microprocessor 65 now sets the digital-to-analog converter 61 to zero, which turns-off the light emitting diode 30 and reads the output of the analog-to-digital converter 75 to measure the dark current voltage of the phototransistor 35. The dark current measurement of the phototransistor 35 is also recorded in the electrically eraseable programmable read/only memory 80 and is used for comparison with future dark current measurements to make adjustments for aging and temperature. The microprocessor 65 flashes a light emitting diode to inform the operator that the calibration in air has been completed. The operator then turns-off the first switch.

The operator now places the light variable loop 26 in water and turns-on a second switch to instruct the microprocessor 65 to calibrate the placement of the light variable loop 26 in water. The microprocessor 65 sets the digital-to-analog converter 61 so that the current flow in the light emitting diode 30 is the same as the current flow therein when the light variable loop 26 was disposed in air. The microprocessor 65 now reads the output of the analog-to-digital converter 75, which reading is stored in the electrically eraseable programmable read/only memory 80. The reading so stored in the electrically eraseable programmable read/only memory 80 serves as the calibration value for water. A light emitting diode is flashed by the microprocessor 65 to inform the operator that the calibration for water has been completed. The operator then turns-off the second switch.

The operator now places the light variable loop 26 in gasoline and turns-on a third switch to instruct the microprocessor 65 to calibrate the placement of the light variable loop 26 in gasoline. The microprocessor 65 sets the digital-to-analog converter 61 so that the current flow in the light emitting diode 30 is the same as the current flow therein when the light variable loop 26 was disposed in air. The microprocessor 65 now reads the output of the analog-to-digital converter 75, which reading is stored in the electrically eraseable programmable read/only memory 80. The reading so stored in the electrically eraseable programmable read/only memory 80 serves as the calibration value for gasoline. A light emitting diode is flashed by the microprocessor 65 to inform the operator that the calibration for gasoline has been completed. The operator then turns-off the third switch.

The calibration procedure is repeated for each liquid or fluid as desired. The microprocessor 65 calculates the threshold values used to differentiate between readings from the analog-to-digital converter 75 to differentiate between various liquids and various fluids. The threshold values can be adjusted to minimize the effects of temperature, aging, supply voltage, and the like. Generally, the threshold values can be established and set mid-way between two calibration readings for the two fluids. When the operator turns-off the sixth switch, the microprocessor 65 returns to the beginning of its main waiting loop.

Figure 7:
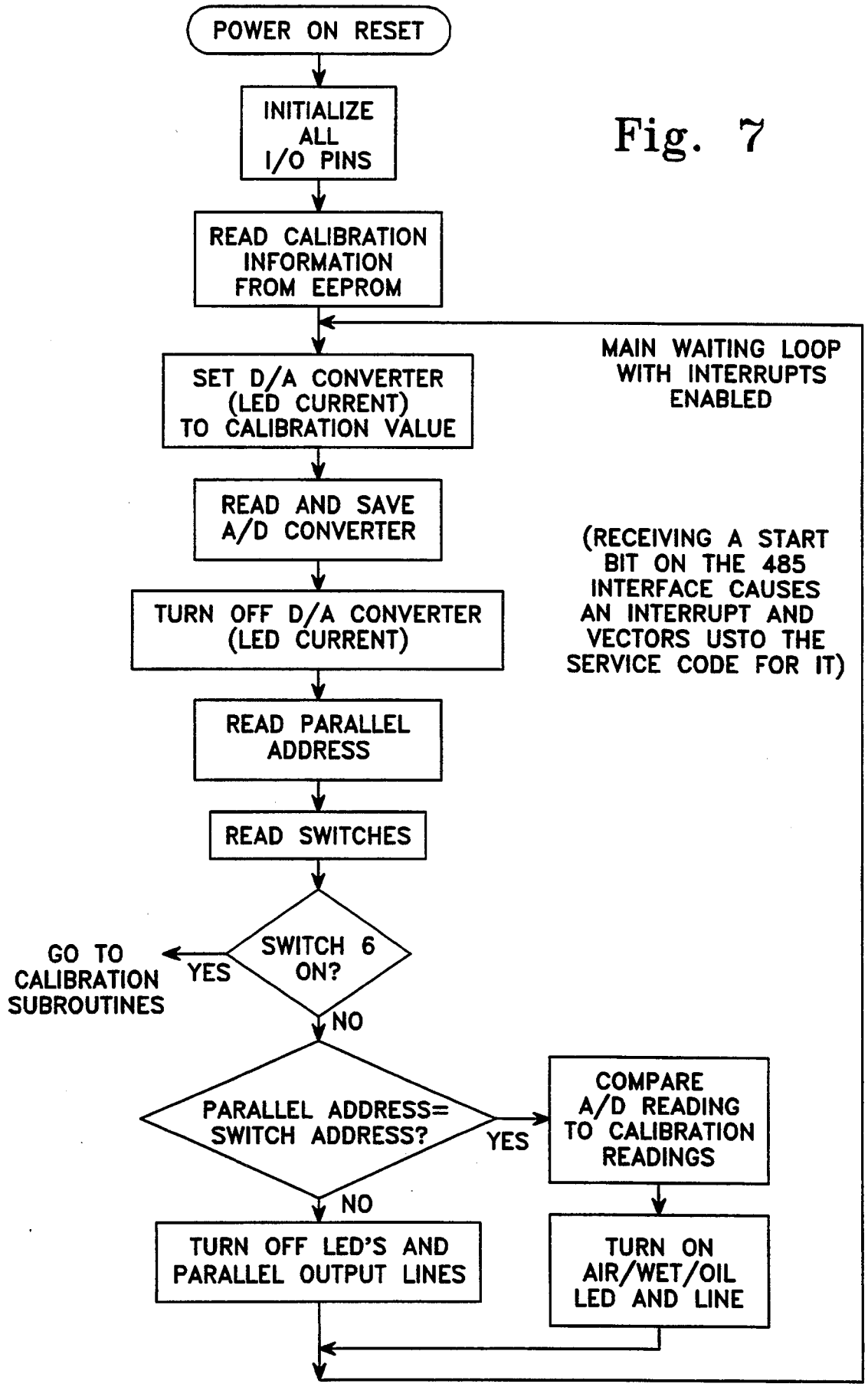
FIG. 7 is a flow diagram of the power-on initialization and the main waiting loop routines for the operation sequence of the electronic circuit shown in FIGS. 4 and 5.

Illustrated in FIG. 7 is the flow diagram for the operation sequence of the power-on initialization and main waiting loop for the circuit illustrated in FIGS. 4 and 5. Upon power-on, or upon a hang condition detected by a watchdog timer, the microprocessor 65 is vectored to the power-on initialization. Interrupts are disabled during this time. The microprocessor 65 first initializes all I/O pins thereon to be used as input or output terminals and sets them to their inactive states. The operating mode for the timer is set to provide periodic interrupts. The timeout for the watchdog timer is set. Diagnostics are run on the microprocessor 65.

A random access memory of the microprocessor 65 is loaded with the default values for the digital-to-analog converter 61 and the nominal values for the analog-to-digital converter 75 for the liquids and fluids to be detected. The microprocessor 65 reads the first two locations in the electrically eraseable programmable read/only memory 80 and looks for the specific hexadecimal value that was written by the microprocessor 65 into the electrically eraseable programmable read/only memory 80 to indicate the completion of the calibrations. Should the microprocessor 65 locate the hexadecimal value in the first two locations of the electrically eraseable programmable read/only memory 80, the microprocessor 65 reads the actual calibration value for the analog-to-digital converter 75 for the liquids and fluids under test and then stores them in the random access memory of the microprocessor 65. The microprocessor 65 uses the default or calibration values to calculate the air to water threshold and the water to gasoline threshold. The threshold values are stored in the aforementioned random access memory. At this point, the microprocessor 65 leaves the initialization operations and enters into the main waiting loop.

As the microprocessor 65 enters into the main waiting loop, the microprocessor 65 sets the digital-to-analog converter 61 to its calibration value and reads the analog-to-digital converter 75. This reading is stored in the random access memory of the microprocessor 65. The microprocessor 65 clears the digital-to-analog converter 61 to turn-off the light emitting diode 30 to minimize power consumption. The microprocessor 65 reads the parallel address and the address switches 91 and stores the same in the random access memory of the microprocessor 65. If the sixth switch is on and the first through the fifth switches are off, the microprocessor 65 enters the calibration subroutines, which were above-described.

If the bits of the parallel address matches the address switches 91, then the address is selected. After the address is selected, the microprocessor 65 compares the readings from the analog-to-digital converter 75 with the air/water threshold value and the water/gasoline threshold value and turns-on the appropriate air, water or gasoline signal on the parallel interface. The microprocessor 65 performs this operation also when the parallel address is zero. If there is no matching parallel address, the microprocessor 65 turns-off all output signal lines on the parallel interface. The microprocessor 65 returns to read the output of the analog-to-digital converter 75. In order to minimize power consumed by the light emitting diode 30, the analog-to-digital converter 75 is not read each time through the light variable loop 26, but is read whenever the Real Time Interrupt Flag has been set by the free running timer.

Interrupts are enabled in the main waiting loop. The microprocessor 65 never leaves the light variable loop 26 except to service interrupts caused by receiving a start bit on the RS-485 serial communications interface.

Figure 8:
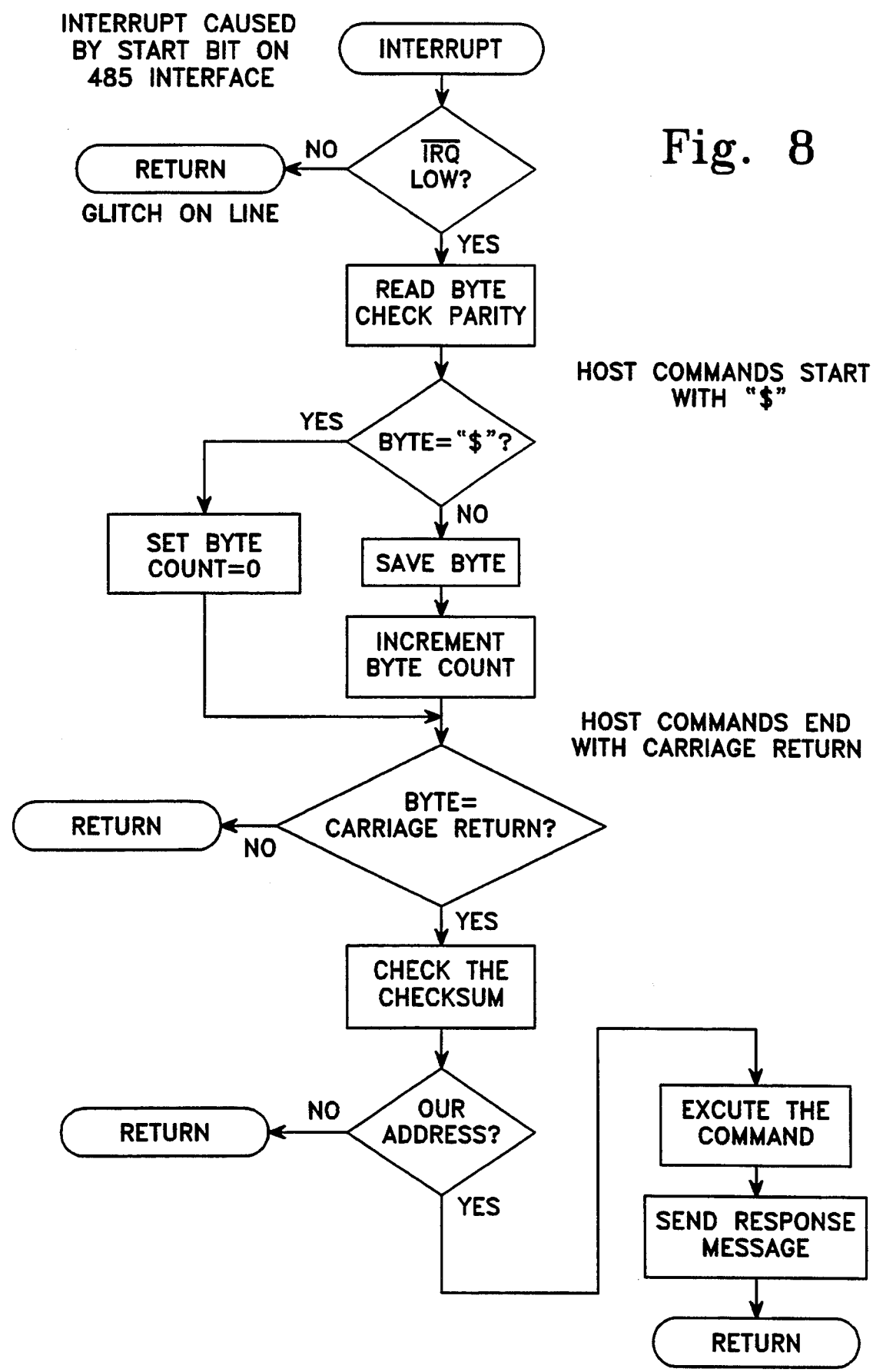
FIG. 8 is a flow diagram of the interrupt routines for the operation sequence of the electronic circuit shown in FIGS. 4 and 5.

Illustrated in FIG. 8 is the operation sequence between the host system and the interface 85. The RS-485 interface 85 provides a serial data communication link between the host system and the RS-485 transceiver 86. Data is transferred in half-duplex at 19,200 BAUD. Data is transferred asynchronously and each character consists of a low going start bit, a 7-bit ASCII encoded character sent least significant bit first, an odd parity bit, and a high stop bit. All communications on the link are controlled by polling from the host system. The interface 85 responds only when addressed by the host system sending an ASCII encoded command addressed to one of the attached probes. Only the addressed probe will execute the command string and will send an ASCII encoded response string back to the host system. All command strings start with an ASCII "$", contain an address byte encoded as two ASCII characters, contain a command code byte encoded as two ASCII characters, multiple ASCII encoded data bytes or characters, a checksum byte encoded as two ASCII characters, and are terminated with an ASCII Carriage Return. Response strings are similar, except that they start with an ASCII "&" instead of a "$".

The received data line from the RS-485 serial communication interface is connected to the IRQ pin on the microprocessor 65. The microprocessor 65 is interrupted by the low going start bit at the beginning of each byte received by the interface 85. This interrupt vectors the microprocessor 65 to a service routine to read in the byte and to determine what action should be taken.

Spurious interrupts may be caused by glitches on the received data line or by data bits being sent back and forth. The microprocessor 65 checks to see if the IRQ line is low, and if it is not, the microprocessor 65 recognizes a glitch or a pending interrupt caused by the transfer of earlier data bits. The microprocessor 65 immediately returns to the initial state should the IRQ line not be in a low state. If the IRQ line is low, the microprocessor 65 recognizes a valid start bit and reads in the byte. The microprocessor 65 checks the byte for correct parity.

The microprocessor 65 compares the byte to the ASCII "$", which is the character sent at the beginning of every command sequence from the host system. If it is an ASCII "$", the microprocessor 65 clears its command byte count that it stores in the random access memory of the microprocessor 65 for noting the beginning of a command string. If it is not an ASCII "$", the microprocessor 65 saves the byte in the random access memory thereof as part of the command string and increments the byte count. If the byte count recognized by the microprocessor 65 is larger than the longest allowed command string (16 bytes in the exemplary implementation), then the byte is not saved. When the byte is saved, microprocessor 65 returns from the interrupt to the main waiting loop.

The microprocessor 65 continues in this fashion until the incoming byte is an ASCII Carriage Return, which signifies the end of a command string. Upon receiving the ASCII Carriage Return, the microprocessor 65 checks to make sure that the checksum appended to the command string is correct. If it is not, the microprocessor does not respond to the command string.

The microprocessor 65 now examines the ASCII address characters, which immediately follow the ASCII "$", and compares the address to its internal address switches 1 to 5. If the address matches, or if the incoming address is zero, then the microprocessor 65 will execute the command string and will send a response to the host system through the RS-485 interface. If the address does not match, then the microprocessor 65 will ignore the command string and will set its byte count to a hexadecimal flip-flop.

The execution of the command may call for reporting the readings of the analog-to-digital converter 75 or the calibration values to the host system, or for calibrating or resetting the interface address. Responses from the interface address to the host system always begin with an ASCII "&", always contain the responding interface address, the command code being executed, any data requested, a checksum byte encoded into two ASCII characters, and are always terminated by an ASCII Carriage Return.

The fiber optic detection system 10 is self-checking by virture of the light variable loop 26 and the electronic circuit 60. In the event the optical connection between the optic fiber element 25 and the electronic circuit 60 is interrupted, severed or degraded in a way that causes light to be lost in its return path to the phototransistor 35, then the fiber optic detection system 10 will either signal an alarm signal, or cause a drifting toward water or hydrocarbon indication if degradation in the optic fiber element 25 occurs.

The fiber optic detection systerm 10 signals an alarm condition should a failure occur in the optic fiber element 25 or in the electronic circuit 60. The failures include, optic fiber element 25; driver circuit, amplifiers 66, for the light emitting diode 30; and power interruption. Degradation of components may cause an intermediate reading between air and water, or between water and hydrocarbon when the analog data is interpreted by the host system.

In the preferred embodiment of the present invention, the operation of the light emitting diode 30 is in an on-state for a period of sufficient time to perform the intended operation of the fiber optic detection system 10 and then is turned-off to conserve energy. During the operation of the fiber optic detection system 10, there are predetermined time intervals for the alternating on and off state of the light emitting diode 30. In the exemplary embodiment of the present invention, the light emitting diode 30 is alternately turned-on and turned-off under the control of the microprocessor 65. The microprocessor 65, in the exemplary embodiment, causes the light emitting diode 30 to be turned-on for approximately 700 microseconds, a period of time deemed sufficient for all the transients to die out; for the electronic circuit 60 to reach steady state; and for the measurements to be made. The time period for the off-state of the light emitting diode 30 is determined by the frequency at which measurements need to be updated for a particular application or purpose for the fiber optic detection system.

What is claimed is:

1. A fiber optic detecting system comprising:
   (a) an optic fiber element having intermediate the ends thereof a continuous light variable section;

(b) a source of light disposed at one end of said optic fiber element for providing light for conduction through said optic fiber element; and (c) a light detector disposed at the other end of said optic fiber element for detecting the quantum of light passing through said light variable section and producing an output signal representative of the quantum of light detected;

(d) said light variable section being adapted to be disposed in a medium and the quantum of light travelling from said light variable section to said light detector being dependent on the light absorption characteristics of the medium in which said light variable section is disposed, said light detector producing a signal representative of the medium in which said light variable section is disposed; and (e) an electronic circuit having a microcomputer connected to said light detector and responsive to the output signal of said light detector for measuring the quantum of light resulting from the light absorption characteristics of the medium in which said light variable section is disposed for determining the medium in which said light variable section is disposed.

2. A fiber optic detection system as claimed in claim 1 in which said optic fiber element is a single optic fiber element.

3. A fiber optic detection system as claimed in claim 1 wherein said light variable section is a light variable loop.

4. A fiber optic detection system as claimed in claim 2 wherein said light variable section has the configuration of a light variable loop.

5. A fiber optic detection system as claimed in claim 3 wherein said optic fiber element has a U-shaped configuration with downwardly extending legs, said light variable loop of said optic fiber element being adjoined to the lower ends of said legs.

6. A fiber optic detection system as claimed in claim 4 wherein said optic fiber element has a generally U-shaped configuration with downwardly extending legs, said light variable loop of said optic fiber element being adjoined to the lower ends of said legs.

7. A fiber optic detection system as claimed in claim 5 wherein said light variable loop has an arcuate section with radii of predetermined dimension.

8. A fiber optic detection system as claimed in claim 6 wherein said light variable loop has an arcuate section with radii of predetermined dimension.

9. A fiber optic detection system as claimed in claim 7 wherein said optic fiber element comprises opaque means surrounding said legs.

10. A fiber optic detection system as claimed in claim 8 wherein said optic fiber element comprises opaque means surrounding said legs.

11. A fiber optic detection system as claimed in claim 1 wherein said microcomputer is connected to said source of light and said light detector for regulating the intensity of light emitted by said source of light and for measuring the quantum of light detected by said light detector for determining the medium in which said light variable section is disposed.

12. A fiber optic detection system as claimed in claim 11 wherein said electronic circuit comprises a digital-to-analog converter interconnecting said microcomputer and said source of light to adjust the intensity of light emitted by said source of light and an analog-to-digital converter interconnecting said light detector and said microcomputer for measuring the quantum of light detected by said light detector, said microcomputer in responding to the signal representing the quantum of light from said analog-to-digital converter determines the medium in which said light variable section is disposed.

13. A fiber optic detection system as claimed in claim 12 wherein said electronic circuit comprises memory means connected to said digital-to-analog converter and said analog-to-digital converter for recording the input signals to said digital-to-analog converter adjusting the light intensity of said source of light and for recording the output signal of said analog-to-digital converter to measure the quantum of light detected by said light detector.

14. A fiber optic detection system as claimed in claim 3 wherein said microcomputer is connected to said light detector for detecting the quantum of light escaping through said light variable loop to determine the medium in which said light variable loop is disposed.

15. A fiber optic detection system as claimed in claim 3 wherein said microcomputer is connected to said light detector for detecting the quantum of light escaping through said light variable loop to determine the medium in which said light variable loop is disposed, the loss of light being commensurate with the light refraction characteristic of said medium.

16. A fiber optic detection system as claimed in claim 3 wherein said light variable section has a curved configuration and the light escaping through said light variable loop is related to the curvature of said light variable section and the light refraction characteristic of the medium in which said light variable section is disposed.

17. A fiber optic detection system as claimed in claim 4 wherein said light variable section has a curved configuration and the light escaping through said light variable loop is related to the curvature of said light variable section and the light refraction characteristic of the medium in which said light variable section is disposed.

18. A fiber optic detection system as claimed in claim 14 wherein said detection of the quantum of light escaping from said variable loop enables said microcomputer to measure the index of refraction of the medium in which said light variable loop is disposed.

19. A fiber optic detection as claimed in claim 15 wherein said detection of the quantum of light escaping from said variable loop enables said microcomputer to measure the index of refraction of the medium in which said light variable loop is disposed.

20. A fiber optic detection system as claimed in claim 3 and comprising a protective cover in which said light variable loop is disposed for protecting said light vaiable loop against marring, said protective cover being formed with openings therein to dispose said light variable loop in the medium.

21. A fiber optic detection system as claimed in claim 4 and comprising a protective cover in which said light variable loop is disposed for protecting said light variable loop against marring, said protective cover being formed with openings therein to dispose said light variable loop in the medium.

22. A fiber optic detection system as claimed in claim 1 wherein said microcomputer is connected to said source of light for turning said source of light alternately on and off in predetermined time intervals.

23. A fiber optic detection system as claimed in claim 1 and comprising cladding surrounding said light variable section.

24. A fiber optic detection system as claimed in claim 1 wherein said optic fiber element has downwardly extending legs and said light variable loop of said optic fiber element being adjoined to the lower ends of said legs, said fiber optic detection system comprising cladding disposed around said legs and said light variable section, said fiber optic detection system comprising a protective cover surrounding the cladding disposed around said legs.

* * * * *